United States Patent
Marticke et al.

(10) Patent No.: US 10,121,561 B2
(45) Date of Patent: Nov. 6, 2018

(54) COLLIMATOR FOR X-RAY DIFFRACTION SPECTROSCOPY, ASSOCIATED DEVICE AND ITS USE

(71) Applicant: Commissariat a l'energie atomique et aux energies alternatives, Paris (FR)

(72) Inventors: Fanny Marticke, Grenoble (FR); Guillaume Montemont, Grenoble (FR); Caroline Paulus, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 195 days.

(21) Appl. No.: 15/337,654

(22) Filed: Oct. 28, 2016

(65) Prior Publication Data
US 2017/0125133 A1 May 4, 2017

(30) Foreign Application Priority Data
Oct. 30, 2015 (FR) ...................... 15 60443

(51) Int. Cl.
*G01N 23/20* (2018.01)
*G21K 1/02* (2006.01)
(Continued)

(52) U.S. Cl.
CPC ............ *G21K 1/025* (2013.01); *G01N 23/087* (2013.01); *G01N 23/20091* (2013.01); *G01N 2223/05* (2013.01)

(58) Field of Classification Search
None
See application file for complete search history.

(56) References Cited

U.S. PATENT DOCUMENTS

2011/0188632 A1* 8/2011 Harding ............... G01V 5/0016
378/86
2013/0294582 A1* 11/2013 Tsujii ....................... A61B 6/06
378/150

FOREIGN PATENT DOCUMENTS

| DE | 23 51 450 A1 | 4/1975 |
| FR | 1561351 | 3/1969 |
| WO | WO 97/33141 | 9/1997 |

OTHER PUBLICATIONS

Mohamed H. Abdelkader, et al., "Development and characterization of a laboratory based X-ray diffraction imaging system for material and tissue characterization", Applied Radiation and Isotopes, 2012, 6 pgs.

(Continued)

*Primary Examiner* — Hoon Song
(74) *Attorney, Agent, or Firm* — Oblon, McClelland, Maier & Neustadt, L.L.P.

(57) ABSTRACT

The invention relates to the field of the analysis of objects by x-ray diffraction spectroscopy. One subject of the invention is a device for analyzing an object by x-ray diffraction spectroscopy, comprising a collimator the shape of which allows various portions of an object to be analyzed simultaneously. To do this, the collimator includes channels inclined with respect to an axis, called the central axis of the collimator, in such a way that various channels address various elementary volumes distributed through the object. Another subject of the invention is a method allowing an object to be analyzed using such a device. The object may for example be a biological tissue that it is desired to characterize non-invasively and non-destructively.

15 Claims, 8 Drawing Sheets

(51) Int. Cl.
    *G01N 23/087*    (2018.01)
    *G01N 23/20091*  (2018.01)

(56) References Cited

OTHER PUBLICATIONS

A. Chaparian, et al., "The optimization of an energy-dispersive X-ray diffraction system for potential clinical application", Applied Radiation and Isotopes, 2010, 9 pgs.

Emily Cook, et al., "Energy dispersive X-ray diffraction as a means to identify illicit materials: A preliminary optimisation study", Applied Radiation and Isotopes, 2007, 9 pgs.

S. Pani, et al., "Characterization of breast tissue using energy-dispersive X-ray diffraction computed tomography", Applied Radiation and Isotopes, 2010, 8 pgs.

D. M. Cunha, et al., "Diffraction enhanced breast imaging through Monte Carlo simulations", Nuclear Instruments and Methods in Physics Research A, 2011, 5 pgs.

Catharine H. Malden, et al., "A CdZnTe array for the detection of explosives in baggage by energy-dispersive X-ray diffraction signatures at multiple scatter angles", Nuclear Instruments & Methods in Physics Research Section A, 2000, 8 pgs.

\* cited by examiner

COLLIMATOR FOR X-RAY DIFFRACTION SPECTROSCOPY, ASSOCIATED DEVICE AND ITS USE

TECHNICAL FIELD

The technical field of the invention is the characterization of an object by spectroscopic analysis of ionizing radiation diffracted by said object. The invention also applies to the analysis of biological tissues, for diagnostic purposes, and also to the non-destructive inspection in the industrial domain or for security-related applications.

PRIOR ART

X-ray diffraction spectroscopy, more widely known by the acronym EDXRD (for energy dispersive X-ray diffraction), is a non-destructive analysis technique frequently used to identify the materials making up an object. This technique is based on elastic scattering of ionizing electromagnetic radiation, also referred to as Rayleigh scattering. It has already been applied to the inspection of nuclear materials, and to the detection of explosives or other illicit substances. Generally, this technique consists in irradiating an object using polyenergetic x-ray radiation and in determining the energy spectrum of the radiation scattered, by the object, at small angles, typically ranging between 1° and 20°, to the path of the x-ray radiation incident on the object. Analysis of this spectrum allows the materials making up an object to be identified. Specifically, most materials have a set spectral signature that depends on their atomic or molecular structure. Comparison of the measured scattering spectra with signatures of known materials allows the composition of the object to be deduced.

In devices known at the present time, a radiation source produces polyenergetic x-ray radiation, the radiation propagating towards an object, a primary collimator, or pre-collimator, being placed between the source and the object so as to direct finely collimated x-ray radiation towards the object. A second collimator is then placed between the analysed object and a detector, the latter being able to acquire an energy spectrum of the radiation scattered by the object. Various forms of this second collimator have been proposed. It may be a question of:
- a simple aperture made in a dense material, as described in patent application WO2013098520; the sensitivity of the measurement is limited by the size of said aperture, the latter acting in the same way as a pinhole camera for optical applications;
- channels extending parallel to one another, as described in U.S. Pat. No. 7,835,495B2; this considerably limits the angular range addressed by the device;
- channels all converging towards the same point, as described in the publication by Malden, "A CdZnTe array for detection of explosives in baggage by energy-dispersive X-ray diffraction signatures at multiple scattering angles", Nuclear Instruments and Methods in Physics Research A (2000). This technique is sensitive, but requires a point-by-point scan of the examined object.

Recent studies have demonstrated that x-ray diffraction spectroscopy is potentially usable in the field of medical diagnostics to discriminate healthy tissue from a cancerous tumour. Specifically, studies have demonstrated that the signature of a healthy tissue is different from the signature of a tumour. In mammography for example, in the publication "X-ray scatter signatures for normal and neoplastic breast tissue" Physics in Medicine and Biology, No. 44, 1999, pp 1791-1802, Kidane, G et al. established that there is a clear difference between the x-ray diffraction spectra obtained from healthy tissues, fibroglandular tissues and a malignant carcinoma, respectively. The healthy or fibroglandular tissues exhibited a peak at about 1.1 $nm^{-1}$, whereas the cancerous tissues had a peak at about 1.6 $nm^{-1}$. The unit $nm^{-1}$ expresses a momentum transfer value, which is obtained, knowing the energy of the scattered radiation and its scattering angle, according to known principles that are recalled below.

However, potential applications to living beings run up against difficulties related to the integrated dose and the duration of an examination. Specifically, at a time when the optimization of the dose received by a patient is becoming a major preoccupation, it is necessary to provide an analysis method allowing a compromise to be obtained between sensitivity and integrated dose. Furthermore, the tissues analysed may occupy a substantial volume, and it is necessary that the volume analysed, in a single acquisition, be optimal so as to limit as much as possible scanning about an organ to be examined. The invention meets these requirements.

SUMMARY OF THE INVENTION

One subject of the invention is a device according to the appended claims. Basically, the device comprises:
- a radiation source configured to produce ionizing electromagnetic radiation, the radiation propagating towards a holder, the holder being able to hold the object;
- a first collimator, placed between the radiation source and the holder, the first collimator having an aperture configured to form a collimated beam propagating along a propagation axis towards the holder;
- a detector, comprising pixels, each pixel being able to detect ionizing electromagnetic radiation and to form therefrom an energy spectrum;
- a second collimator, placed between the holder and the detector, the second collimator being configured to selectively direct radiation emitted by the object, which is held by the holder, towards said detector, depending on a scattering angle of the radiation emitted by the object.

The second collimator extends, between a first end and a second end, around a central axis, the second collimator comprising a plurality of channels, each channel being bounded by lateral walls, the second collimator being such that:
- each channel has a median axis, the median axis extending, in the centre of the channel, between said lateral walls bounding the channel;
- the median axis of each channel makes an acute angle, called the collimating angle of the channel, with the central axis of the second collimator;
- each channel being associated to a point, called the focal point, formed by an intersection between the median axis of the channel and the central axis of the second collimator;
- the second collimator comprising at least two channels, the collimating angles of which are different, the focal points respectively associated with these channels being different and spaced apart from each other along the central axis of the second collimator;
- such that each channel transmits to the detector a radiation emitted by an elementary volume of the object, which is placed on the holder, extending around a focal point defined by the second collimator, in a preset angular range.

The second collimator, when placed between an object irradiated by ionizing electromagnetic radiation and a detector, allows radiation emitted by the object, and especially radiation scattered at various angles, to be transmitted to the detector. Moreover, providing a plurality of different focal points allows radiation emitted by various portions of the object to be detected simultaneously. When the radiation emitted is scattered radiation, this allows these various portions to be characterized simultaneously without having to move the collimator relative to the object. Thus, each channel of the second collimator transmits to the detector radiation emitted by an elementary volume of the object, which is placed on the holder, said elementary volume extending around a focal point defined by said second collimator, in a preset angular range.

At least two focal points are spaced apart from each other, along said central axis of the collimator, by a distance larger than 2 cm, or even 4 cm.

The second collimator may include what is called a base wall, extending around the central axis and describing a cylinder or a conical frustum, of thickness larger than 5 mm. This base wall may be solid or include a hollow cavity, extending along a median axis coincident with the central axis of the collimator.

The device may have one of the following features, which may be implemented singly or in the technically possible combinations:
- the ionizing radiation emitted by the source is polyenergetic radiation, the source for example being an x-ray tube.
- The second collimator is placed such that its central axis is coaxial with the propagation axis of the collimated incident beam.
- The detector extends in a plane, called the detection plane, perpendicular to said central axis of the second collimator. A plurality of pixels are then placed at the same distance, called the radial distance, from said central axis of the second collimator.
- The detector is connected to a computer, such as a microprocessor, able to subdivide each pixel of the detector into what are called virtual pixels.

It is preferable for the features mentioned in the four preceding points to be combined.

The device may include an object to be analysed, which is placed on the holder, such that at least one focal point, and preferably a plurality of focal points, which points are defined by the second collimator, are placed in the object.

Another subject of the invention is a method for analysing an object according to one of the appended claims, using a device according as described in this specification. The method may comprise the following steps:
a) placing the object on the holder of the device and irradiating the object using the irradiation source, so as to form a collimated incident beam propagating towards the object along a propagation axis, the object being placed such that a plurality of focal points, which are defined by the second collimator, are placed in said object;
b) using each pixel of the detector, detecting radiation scattered by the object following its radiation by said collimated incident beam and forming a spectrum representative of the energy distribution of said detected radiation;
c) defining a plurality of groups of pixels, each group of pixels receiving radiation scattered by a given volume element of the object, the volume element being located on the propagation axis, two different groups of pixels receiving radiation scattered by two different volume elements;
d) for each group of pixels defined in the preceding step, combining the spectrum acquired by each pixel, so as to establish a spectrum, called the combined spectrum, associated with said group of pixels; and
e) using the combined spectra respectively associated with various groups of pixels, determining a nature of the material constituting a plurality of volume elements of the object.

The object may especially be a biological tissue. The invention then allows the nature of the tissue to be characterized non-invasively.

Other advantages and features will become more clearly apparent from the following description of particular embodiments of the invention, which are given by way of nonlimiting example and shown in the appended drawings, which are described below.

FIGURES

FIG. 1A shows an exemplary device for analysing a material according to the invention. FIG. 1B shows a cross-sectional view of a first embodiment of the collimator of the device described with reference to FIG. 1A. The cross-sectional plane is a plane parallel to the central axis of the collimator and passing through this axis. FIG. 1C shows a detail of an elementary volume of an object observed by a channel. FIG. 1D shows the elementary volumes of an object associated with various channels, and a volume element associated with a pixel of the detector. FIG. 1E shows an exemplary detector. FIG. 1F shows an exemplary spectrum of radiation emitted by a radiation source. FIGS. 1G and 1H show cross sections of the first embodiment of the collimator, the sections being perpendicular to the central axis of the collimator.

FIG. 2A shows a second embodiment of the collimator, able to be used in the device shown in FIG. 1A. FIGS. 2B and 2C shows cross-sectional views of this collimator, the cross-sectional planes being perpendicular to the central axis of the collimator. FIG. 2D shows a three-dimensional view of the collimator shown in FIG. 2A. FIG. 2E is a cross-sectional view of the schematic in FIG. 2D, the cross-sectional plane passing through the central axis of the collimator and parallel to this central axis.

DESCRIPTION OF PARTICULAR EMBODIMENTS

Figure 1A:
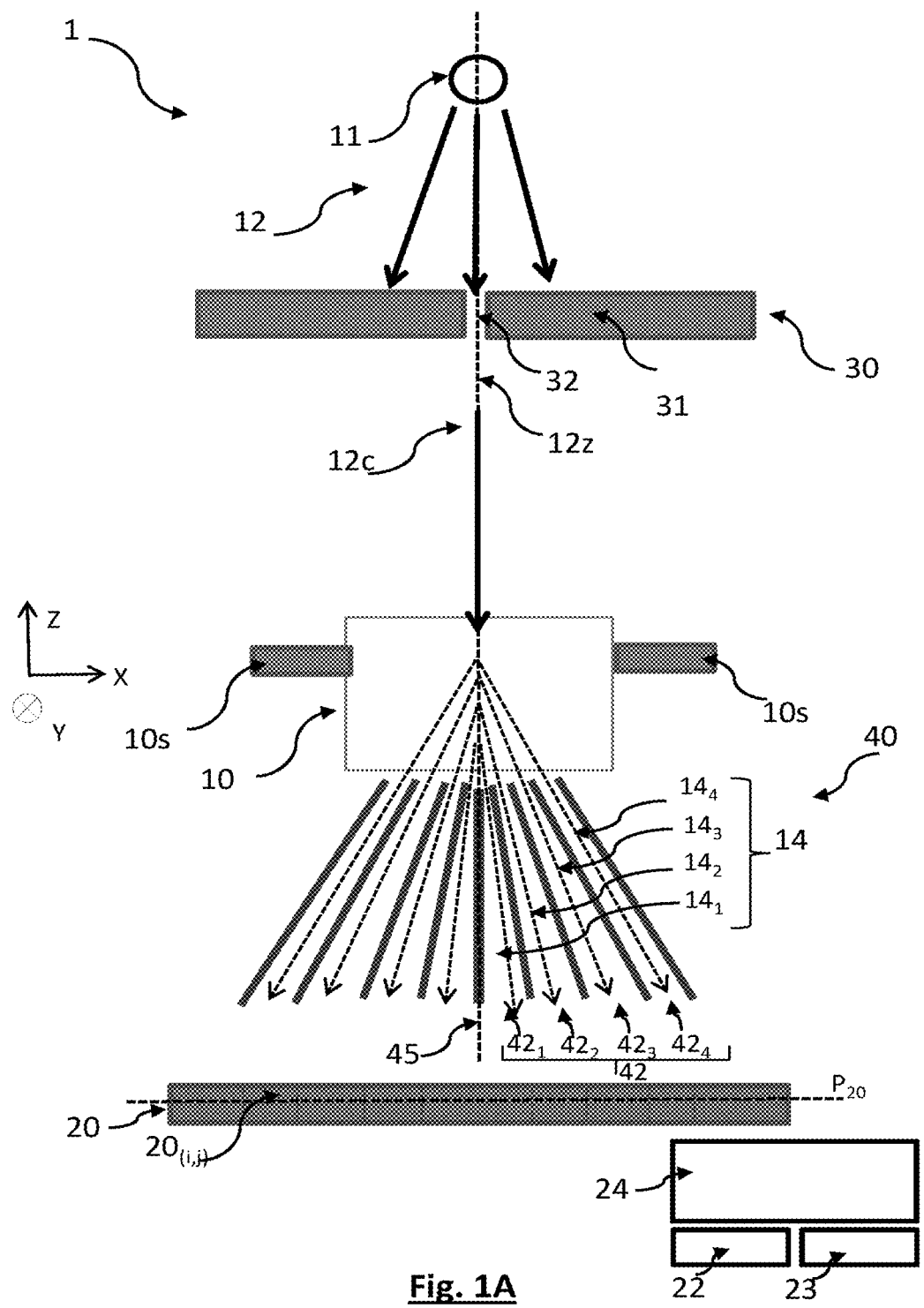

FIG. 1A shows an exemplary device 1 for analysing a material. A radiation source 11 emits ionizing electromagnetic radiation 12, the radiation propagating towards an object 10 the composition of which it is desired to determine. The device comprises a first collimator, or pre-collimator 30, able to collimate the radiation emitted by the radiation source 11 in order to form a collimated incident beam 12c, the beam propagating along a propagation axis 12z towards the object. The device also includes a detector 20, including pixels $20_{i,j}$, each pixel being able to detect radiation 14 transmitted by the object irradiated by the collimated incident beam, this radiation for example being generated by elastic scattering of the radiation forming the collimated incident beam 12c.

The analysing device 1 includes a second collimator 40, which is interposed between the object 10 and the detector 20. This collimator extends around an axis, called the central axis 45. It is able to selectively direct, towards the detector, scattered radiation $14_1$, $14_2$, $14_3$, $14_4$ transmitted by the object 10 depending on an angle $\theta_1$, $\theta_2$, $\theta_3$, $\theta_4$ of propagation of this radiation with respect to the central axis 45. The term "selectively" means that the radiation transmitted towards the detector depends on the angle at which it is propagating and on the portion of the object from which it was emitted. This second collimator, designated by the term collimator in the rest of the text, is a key element of the invention and will be described more precisely below.

The analysing device 1 is placed in a reference frame with which an orthogonal coordinate system X, Y, Z such as shown in FIG. 1A is associated. The object is placed or held on a holder 10s.

The expression "ionizing electromagnetic radiation" designates electromagnetic radiation consisting of photons of energy higher than 1 keV, and preferably lower than 5 MeV. The energy range of the ionizing radiation may be comprised between 1 keV and 2 MeV, but it most often extends between 1 keV and 150 keV or 300 keV. The ionizing radiation may be x-ray or γ-ray radiation. Preferably, the source of ionizing radiation is polyenergetic, the incident radiation being emitted in an energy range generally extending over several tens or even several hundreds of keV. It is especially a an X-ray emitting tube.

The radiation detector is a detector comprising pixels $20_{i,j}$ that are arranged in a plane called the detection plane $P_{20}$. The indices i, j designate the coordinates of each pixel in the detection plane. The pixels may form a linear array but in general they form a two-dimensional regular matrix array. In the examples described in this patent application, the detection plane is an XY plane perpendicular to the central axis 45 of the collimator, the latter axis being coincident with the propagation axis 12z of the collimated incident beam 12c. This is a preferred configuration.

The radiation source 11 is an X-ray tube equipped with a tungsten anode that is subjected to a voltage, generally comprised between 40 and 150 kV, which may be varied in order to modify the energy range of the incident radiation 12. The detector 20 comprises 40 pixels along the X-axis by 40 pixels along the Y-axis, namely 1600 pixels, each pixel having an area of 2.5×2.5 mm², its thickness being 5 mm. Each pixel is made from a semiconductor material, for example CdTe or CdZnTe, or any other material able to produce spectroscopic measurements, preferably at room temperature. It could also be a scintillator material, providing it has a sufficient energy resolution. The detector is resolved in energy, and each pixel allows spectra to be obtained in energy channels of about 1 keV. The radiation source 11 may include a metal screen, for example made of copper, so as to block the propagation, towards the pre-collimator 30, of radiation the energy of which is lower than a threshold, for example 20 keV. When this screen is made of copper, its thickness is for example equal to 0.2 mm.

The first collimator 30, or pre-collimator, includes a block of dense material 31 so as to absorb almost all the radiation 12 emitted by the radiation source 11. It contains a small aperture 32, extending along an axis, called the propagation axis 12z, allowing a narrow collimated beam 12c to pass. By small aperture, what is meant is an aperture the diameter of which or the largest diagonal of which is smaller than 2 cm, or even than 1 cm. In this example, the aperture is a cylinder of 1 mm diameter.

The object 10 may be a living biological tissue, for example a portion of the body of an animal or of a human being. The device is then a medical imaging device. The portion of the body may in particular be an organ in which, following a first examination, for example an X-ray or scan, the presence of an anomaly, in particular a cancerous tumour, is suspected. This first examination also allows an approximate location of the anomaly in the tissue to be determined. The device 1 may then be implemented during a second indication, in order to characterize the nature of the tissues making up the organ in the location of said anomaly and in its vicinity. The organ is especially an organ located on the periphery of the body, so as to allow an easy analysis without being affected by attenuation due to bones or other organs. It may in particular be a breast, a testicle, or an organ of the abdominal cavity. In other applications, the object may also be an industrial part or a piece of luggage, the device 1 then being used for non-destructive inspection purposes.

Each pixel $20_{i,j}$ of the radiation detector 20 includes:
 a detector material, able to interact with the photons of the radiation $14_1$, $14_2$ ... $14_n$ ... $14_N$ transmitted by the object 10, through the second collimator 40, this material being a scintillator material or, preferably, a semiconductor material compatible with use at room temperature, such as CdTe or CdZnTe;
 an electronic circuit, able to generate a signal the amplitude A of which depends on, and is preferably proportional to, an energy E deposited by each photon interacting with the detector material; and
 a spectroscopy circuit, able to establish an energy spectrum, denoted $S_{i,j}$, from the signals detected during a period of time called the period of acquisition.

Thus, when the pixels are regularly arranged in a matrix array, each pixel is able to produce a spectrum $S_{i,j}$ from the radiation 14 transmitted by the object according to this matrix array.

The expression "energy spectrum" corresponds to a histogram of the amplitude A of the signals detected during a period of acquisition of the spectrum. A relationship between the amplitude A of a signal and the energy E of the radiation may be obtained using an energy calibration function g such that E=g(A), according to principles known to those skilled in the art. An energy spectrum $S_{i,j}$ may therefore take the form of a vector, each term of which $S_{i,j}(E)$ represents an amount of radiation detected by the pixel $20_{i,j}$ in an energy range E±δE/2, where δE is the spectral width of an energy discretization step of the spectrum.

The device also comprises a computing unit, or processor 22, for example a microprocessor, able to process each spectrum $S_{i,j}$ measured by the pixels $20_{i,j}$ of the detector 20. In particular, the processor is a microprocessor connected to a programmable memory 23 in which is stored a sequence of instructions for performing the spectra-processing and computing operations described in this description. These instructions may be saved on a storage medium, which is readable by the processor, such as a hard disk, CD-ROM or another type of memory. The processor may be connected to a display unit 24, for example a screen.

The collimator 40 includes channels 42, the channels extending around the central axis 45 and converging towards the latter. More precisely, each channel $42_n$ is able to transmit transmitted radiation $14_n$ at a scattering angle $\theta_n$ belonging to a preset angular range $\Delta\theta_n$, the radiation being transmitted by the object 10 towards the detector 20.

Figure 1B:
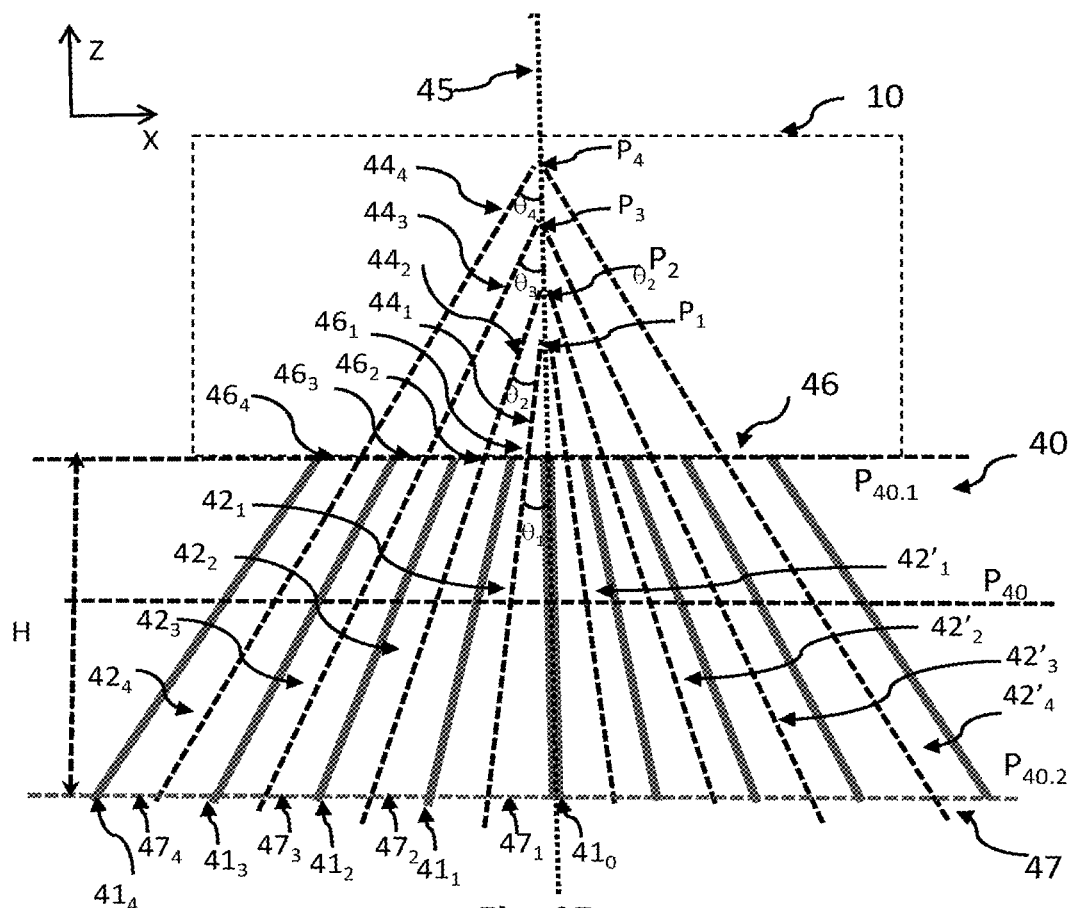

FIG. 1B shows a cross-sectional view of the second collimator 40, the cross-sectional plane being an XZ plane passing through the central axis 45. This central axis extends through the thickness of the collimator 40, in the centre of the latter. The collimator 40 extends between two planes $P_{40.1}$ and $P_{40.2}$ that are perpendicular to the central axis 45. These planes respectively define a first end 46 and a second end 47 of the collimator. It comprises channels $42_1$, $42_2$, $42_3$, $42_4$ each extending respectively between a first end $46_1$, $46_2$, $46_3$, $46_4$ and a second end $47_1$, $47_2$, $47_3$, $47_4$. Each first end is intended to be placed facing the object 10 to be characterized, whereas each second end is intended to be placed facing a detector 20. Preferably, as is shown in FIG. 1B, the collimator 40 is placed, facing the object 10, in such way that the central axis 45 of the collimator 40 is coincident with the axis 12z of the incident collimated beam 12c.

In the rest of the text, n is a natural integer higher than or equal to 1 and lower than or equal to N, N being a strictly positive integer. n designates any channel $42_n$ of the collimator whereas N designates the number of channels of the second collimator. The same goes for the lateral walls $41_n$, which are defined below, or the first ends $46_n$ or $47_n$, the index n referring to the channel $42_n$.

Each channel $42_n$ is bounded by at least two lateral walls $41_{n-1}$, $41_n$, the wall $41_{n-1}$, which is called the proximal wall, being closer to the central axis 45 than the wall $41_n$, which is called the distal wall. Thus, the channels $42_1$, $42_2$, $42_3$ and $42_4$ are respectively bounded by the lateral walls $41_0$ and $41_1$, $41_1$ and $41_2$, $41_2$ and $41_3$, $41_3$ and $41_4$. These lateral walls are produced from a material that is dense enough to significantly attenuate electromagnetic radiation in the emission energy range in which the radiation source 11 emits the incident radiation 12. Metal materials are preferred, and in particular materials the atomic number of which is higher than or equal to that of iron (26), and preferably higher than or equal to that of lead (82). Collimators made of lead or of an alloy mainly containing tungsten are conventionally used for this type of application. The thickness of these walls is generally smaller than 1 cm, or even 0.5 cm. It may vary between the first end and the second end of the collimator 40. Each channel extending between the various walls is filled with a material that does not attenuate much, air for example.

In the example shown, the lateral walls $41_1$, $41_2$, $41_3$, $41_4$ have a substantially frustoconical shape and extend around the central axis 45 of the collimator. The frustoconical shape of each lateral wall $41_n$ may be defined by an apex, located on the central axis 45, and by an annular generatrice extending, at the second end $47_n$ of a channel $42_n$ bounded by said lateral wall, around the central axis of the collimator. Thus in a transverse plane $P_{40}$ extending perpendicularly to the central axis 45, the cross section of each channel describes a portion of a ring the centre of which is located on this central axis. The term ring designates a circular or polygonal ring.

In this example, the collimator includes a central wall, called the base wall, $41_0$ which is solid and the outside radius of which bounds the channel $42_1$. This base wall extends between the central axis of the collimator and the channel that is closest to this central axis. This base wall is cylindrical or frustoconical. It extends around the central axis 45, so as to prevent transmission of radiation transmitted by the object in an incident direction parallel to the axis of propagation $12_z$. According to one variant, whatever the embodiment, the collimator may include a hollow base wall $41_0$. In this case, the base wall extends around the central axis 45, defining a cylinder or a cone, and bounds a cavity the median axis of which is the central axis 45 of the collimator. This allows a measurement, by the detector 20, of a spectrum of the radiation propagating along the central axis 45 after transmission by the object 10. When the central axis of the collimator is coincident with the propagation axis 12z of the incident collimated beam 12c, this allows a measurement, by the detector 20, of the spectrum of radiation transmitted by the object and not deviated by the latter. This allows the attenuation of the collimated radiation 12c which is caused by the object to be estimated.

Each lateral wall extends between an outside radius and/or an inside radius. These radii, at the first end 46 of the collimator, vary between a few millimeters for the wall the closest to the central axis 45 to a few centimeters, for example 1 or 2 cm for the lateral wall furthest from the central axis 45. At the second end 47, these outside radii vary between a few millimeters for the closest wall to a few centimeters, for example 6 cm, for the furthest wall. The aperture of a channel $42_n$, i.e. the distance between the lateral walls bounding it, is for example smaller than 1 mm at the first end $46_n$, and is comprised between 1 mm and 1 cm at the second end $47_n$.

Each channel $42_n$ extends, between its first end $46_n$ and its second end $47_n$, around a median axis $44_n$. FIG. 1B shows the median axes $44_1$, $44_2$, $44_3$ and $44_4$ respectively associated with the channels $42_3$, $42_2$, $42_3$ and $42_4$. By median axis, what is meant is an axis extending along the centre of the channel, i.e. at equal distance from the lateral walls bounding said channel. Each median axis $44_n$ of a channel $42_n$ is inclined with respect to the central axis 45 of the collimator, thus making an acute angle $\theta_n$ called the collimating angle of the channel $42_n$.

FIG. 1B also shows channels $42'_1$, $42'_2$, $42'_3$ and $42'_4$ the collimating angle of which is respectively identical to that of the channels $42_1$, $42_2$, $42_3$ and $42_4$. Thus, in this example, a plurality of channels may have the same collimating angle.

Each median axis $44_n$ of a channel $42_n$ intersects the central axis 45 of the collimator at a point $P_n$ called a focal point. A noteworthy aspect of this collimator is that the focal points $P_1$, $P_2$, $P_3$, $P_4$ associated with channels the respective collimating angles $\theta_1$, $\theta_2$, $\theta_3$, $\theta_4$ of which are different are spaced apart from one another. In other words, and this is a notable difference with respect to the prior art, the channels of the collimator $42_n$ extend around median axes $44_n$ intersecting the central axis 45 of the collimator in such a way that:

the median axes $44_n$, $44'_n$ of two channels $42_n$, $42'_n$ having the same collimating angle $\theta_n$ are secant, and intersect at a same point, called a focal point $P_n$, at the collimating angle $\theta_n$, this point being located along the central axis 45 of the collimator;

the median axes $44_n$, $44_{n'}$ of two channels $42_n$, $42_{n'}$ the collimating angles ($\theta_n$, $\theta_{n'}$) of which are different, intersect the central axis at two different focal points $P_n$, $P_{n'}$ located along the central axis 45 of the collimator.

Each channel $42_n$ is able to transmit radiation $14_n$ transmitted by the object 10 around a focal point $P_n$, said radiation propagating in an angular range $\Delta\theta_n$ extending around the collimating angle $\theta_n$ of the channel. Apart from the collimating angle $\theta_n$, this angular range $\Delta\theta_n$ depends on the diameter of the channel, or its diagonal, and the length of the channel $42_n$ between its first end $46_n$ and its second end $47_n$. The greater this length, the narrower the angular range $\Delta\theta_n$ around the collimating angle $\theta_n$ will be. The smaller the aperture of a channel, the narrower the angular range $\Delta\theta_n$ around the collimating angle $\theta_n$ will be. The aperture of a channel $42_n$ designates the distance between the two proximal and distal lateral walls bounding it.

The fact that the focal points are spaced apart from one another allows various portions of the object 10 to be examined simultaneously. Specifically, as shown in FIG. 1B, the collimator 40 is placed between the object 10 and the detector 20, such that all or some of the focal points $P_1$, $P_2$ ... $P_n$ ... $P_N$ are included in the object 10. Generally, the distance between the focal point closest to the collimator and the focal point furthest from the collimator is comprised between 1 and 100 cm depending on the targeted applications, and preferably between 2 and 50 cm. This corresponds, in FIG. 1B, to the distance between the points $P_1$ and $P_4$. For applications to biological tissues, this distance is comprised between 1 cm and 10 cm and preferably between 2 cm and 10 cm.

Figure 1C:
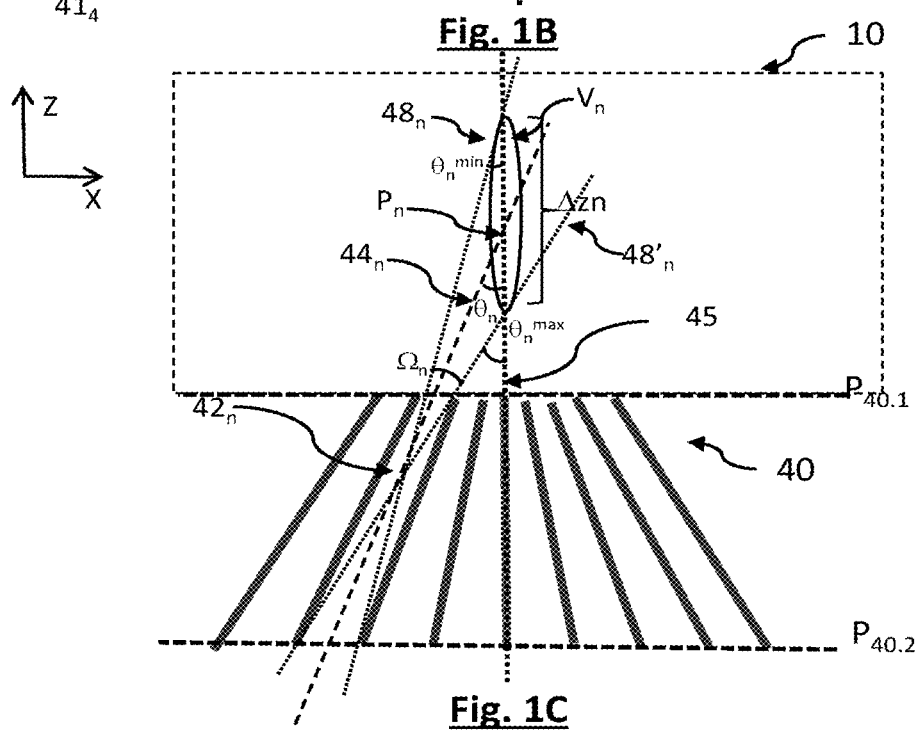

FIG. 1C illustrates the definition of an angular range $\Delta\theta_n$ associated with a channel $42_n$. Because of its aperture, this channel is able to transmit radiation emitted (or transmitted) by the object in an angular range $\Delta\theta_n$ bounded by a minimum collimating angle $\theta_n^{mi}$ and a maximum collimating angle $\theta_n^{max}$. These two limit angles are determined by representing the limits $48_n$, $48'_n$ of the solid angle $\Omega_n$ under which the channel $42_n$ sees the object 10. The intersection of this solid angle $\Omega_n$ with the incident beam 12c allows an elementary volume $V_n$ of the object seen by the channel to be defined. This elementary volume occupies a range of coordinates $\Delta z_n$ along the central axis 45 of the collimator, which range is called the spatial extension associated with the channel $42_n$. For the sake of clarity, the incident beam $12_c$ has not been shown in FIG. 1C. This beam extends along a propagation axis $12_z$, which is in this example coaxial with the central axis 45 of the collimator 40.

Figure 1D:
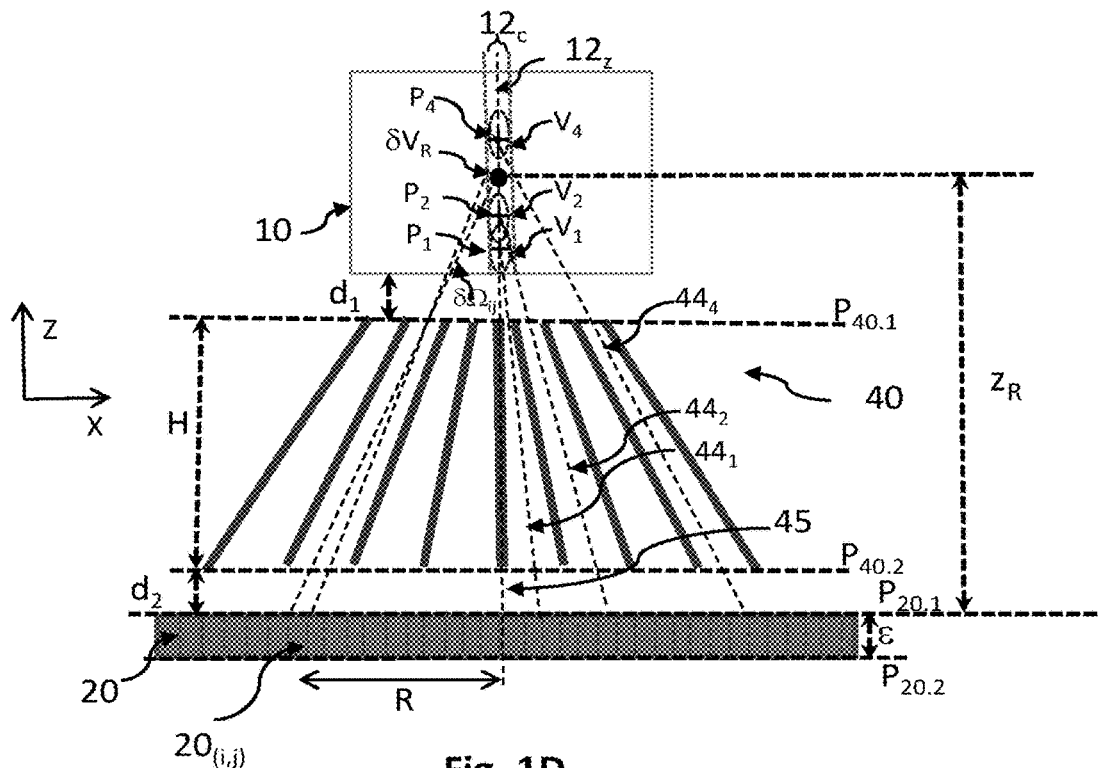

FIG. 1D shows the collimator 40, described with reference to the above figures, placed between an object 10 and a detector 20. The median axes $44_1$, $44_2$, $44_4$ of three channels $42_1$, $42_2$, $42_4$ have been shown, and the respectively associated focal points $P_1$, $P_2$, $P_4$. The elementary volumes $V_1$, $V_2$, $V_4$ of the object 10 addressed by each channel have also been shown. The distribution of the focal points along the central axis 45 allows the various examined elementary volumes to be distributed along this axis. Thus, depending on the channel facing which they are placed, the pixels $20_{i,j}$ of the detector 20 acquire a spectrum of the scattered radiation representative of one or other of these elementary volumes. The channels are preferably arranged such that the elementary volumes overlap as little as possible.

The first and second ends of the collimator respectively correspond, in this example, to the planes $P_{40.1}$ and $P_{40.2}$ between which the collimator 40 extends. They are separated by a height H, called the height of the collimator, generally comprised between 5 and 100 cm and preferably between 5 and 50 cm. The higher it is, the narrower the angular range $\Delta\theta_n$ associated with each channel $42_n$, thereby improving the angular resolution, but the greater the cost, bulk and weight of the collimator.

The distance $d_1$ between the object 10 and the collimator 40 may be adjusted: it may be zero, the collimator making contact with the object. It may also reach a few cm, while usually being less than 10 cm. The same goes for the distance $d_2$ separating the collimator 40 from the detector 20. Generally, the collimator is placed such that a plurality of focal points, and preferably all the focal points, are included in the object 10. In this way, the detector 20 allows transmitted radiation $14_n$ coming from various elementary volumes $V_n$ of the object, each elementary volume extending around a focal point $P_n$, to be detected.

The detector 20 extends between two planes $P_{20.1}$ and $P_{20.2}$, which are preferably perpendicular to the central axis 45 of the collimator 40. Thus, in this example, the detector extends perpendicularly to the propagation axis $12_z$ of the collimated incident beam $12_c$. The thickness s of the detector 20 corresponds to the distance between the two planes $P_{20.1}$ and $P_{20.2}$. It is generally comprised between 1 and 10 mm and, in this example, reaches 5 mm.

Each pixel $20_{i,j}$ of the detector is located at a distance R, called the radial distance, from the central axis 45 of the collimator. When, as in this embodiment, the detector 20 extends perpendicularly to this central axis 45, it is possible to define a group of pixels $20_R$ including all the pixels $20_{i,j}$ that are equidistant from the central axis 45, and therefore from the axis 12z of the collimated beam 12c. A group of pixels $20_R$ then corresponds to pixels $20_{i,j}$ the radial distance R of which is identical. Because of the geometry of the collimator, each group of pixels $20_R$ is associated with one volume element $\delta V_R$ of the object, corresponding to the intersection between the solid angle $\delta\Omega_{i,j}$ under which a pixel $20_{i,j}$ of said group sees the object, with the collimated incident beam 12c. This volume element $\delta V_R$ is defined depending on a distance z between the detector and said volume element, and a scattering angle $\theta_n$.

Figure 1E:
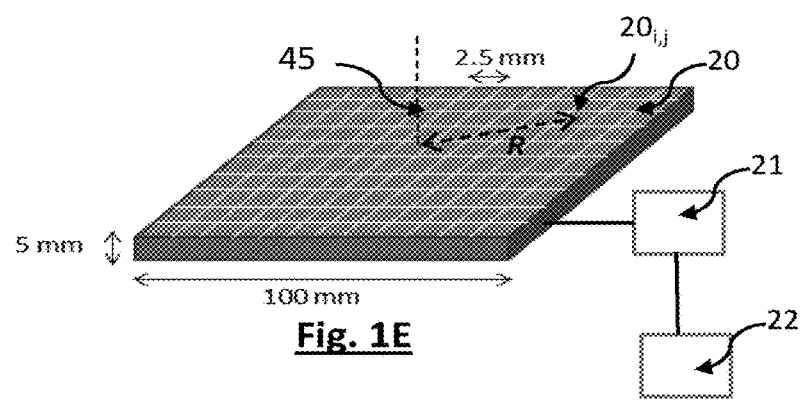

FIG. 1E shows an exemplary detector, including parallelepipedal pixels of 2.5 mm×2.5 mm size and of thickness ε=5 mm, which pixels are arranged in a two-dimensional matrix array of 40 pixels by 40 pixels. The central axis 45 of the collimator 40 is also shown. The useful detection area is therefore 100 mm×100 mm. Each pixel $20_{i,j}$ is connected to an electronic circuit 21 allowing signals representative of the energy of the scattered radiation transmitted by a channel $42_n$ located facing said pixel to be collected. This figure also shows a radial distance R of a pixel $20_{i,j}$. The detector 20 may be connected to a processor 22 (described above) allowing a first processing operation consisting in analysing the signals emitted by a plurality of adjacent pixels, so as to locate the point of impact of detected radiation with a spatial resolution smaller than the pitch with which these pixels are distributed, to be carried out. Such a processing operation, which is known to those skilled in the art as sub-pixelation or sur-pixelation, amounts to forming what are called virtual pixels $20^*_{k,l}$, the area of each virtual pixel possibly for example being 1 mm×1 mm, or even 0.5 mm×0.5 mm. The spatial resolution of the detector 20 is thus increased.

Figure 1F:
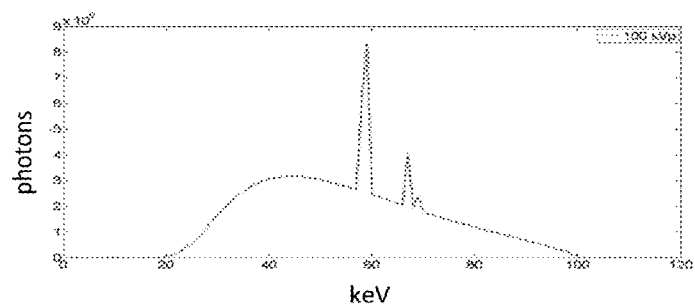

FIG. 1F shows an exemplary spectrum of the radiation 12 emitted by the radiation source 11. This spectrum represents a number of photons (ordinate) as a function of the energy (abscissa). The absence of a significant signal below 20 keV, due to the attenuating copper screen placed as mentioned above, will be noted. The peaks correspond to the x-ray fluorescence peaks of tungsten. It may be seen that the spectral range of this emitted radiation extends between 20 and 100 keV, this not being unconventional for this type of analysis.

Figure 1G:
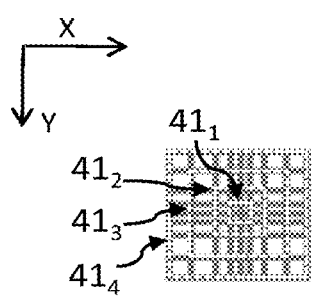
Figure 1H:
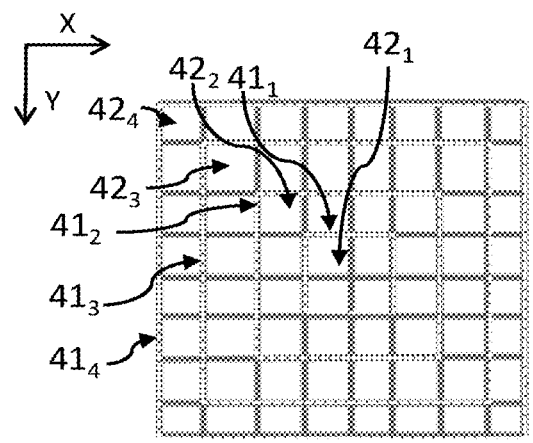

FIGS. 1G and 1H show cross sections of the collimator 40 described above, the cross-sectional planes being the planes $P_{40.3}$ and $P_{40.2}$ shown in FIG. 1D, respectively.

The collimator 40 takes the form of an assembly of plates including apertures, each plate possibly having a thickness of 1 mm. The size of each aperture increases as it gets closer to the plane $P_{40.2}$. Thus, the assembly of plates forms a collimator, each channel of which is formed by the apertures of the plates, which are adhesively bonded to one another. In each of these figures, with white dashed lines, each lateral wall $41_1$, $41_2$, $41_3$, $41_4$ has been shown. In this configuration, each lateral wall describes a square generatrice ring around the axis 45.

FIG. 2A shows another embodiment, in which each channel 42 of the collimator is annular. Thus, in a plane $P_{40}$ extending perpendicularly to the central axis 45, each channel has a cross section describing a ring. The ring may be of polygonal or circular generatrice. Each median axis $44_n$ of each channel $42_n$ lies on a conical surface, lying at equal distance from the lateral walls $41_{n-1}$ and $41_n$ bounding the channel, and the apex of which, included on the central axis 45, corresponds to the focal point $P_n$. In the same way as in the preceding embodiment, to each channel $42_n$ there corresponds a focal point $P_n$ corresponding to the intersection between the median axis $44_n$ with the central axis 45 of the collimator 40.

Figure 2B:
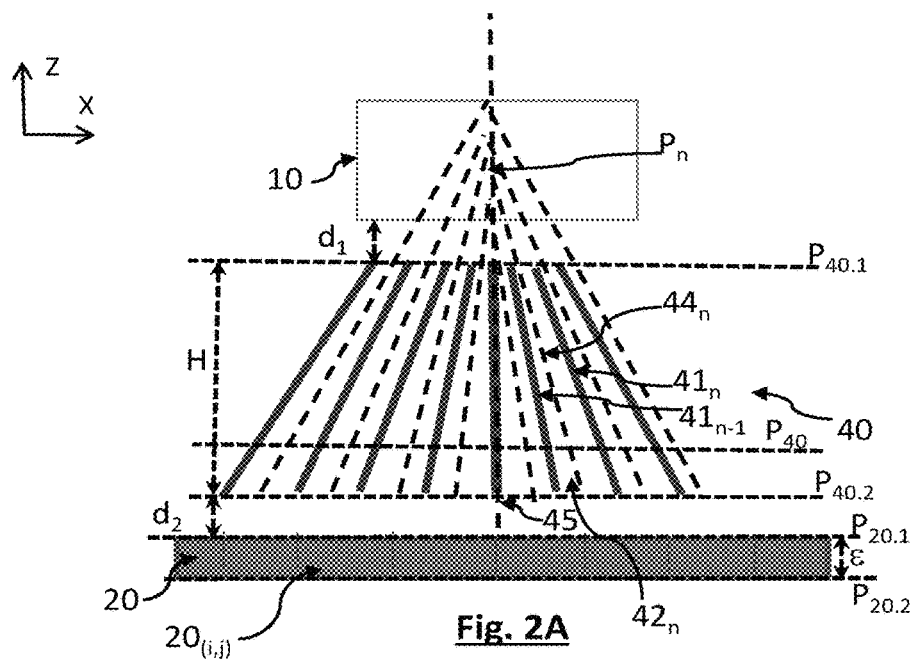
Figure 2B:
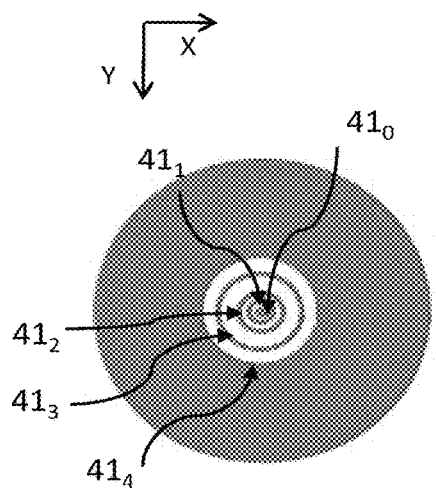
Figure 2C:
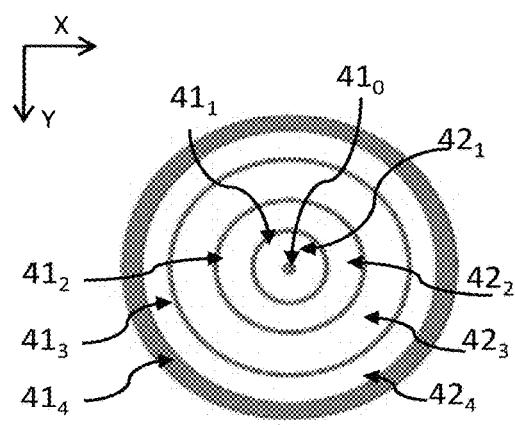

FIGS. 2B and 2C show cross-sectional views of the collimator 40, the respective cross-sectional planes being the planes $P_{40.1}$ and $P_{40.2}$ between which the collimator 40 extends. This allows the annular cross section of each channel to be observed.

Figure 2D:
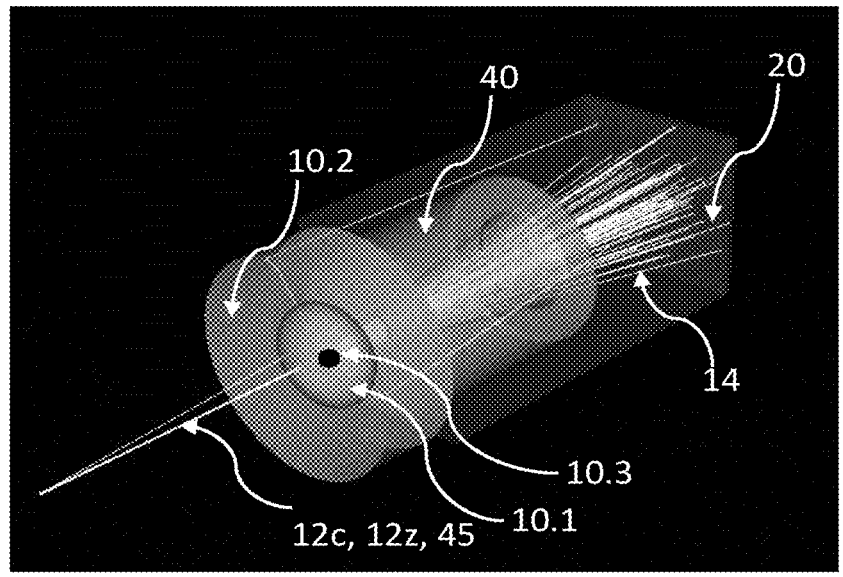
Figure 2E:
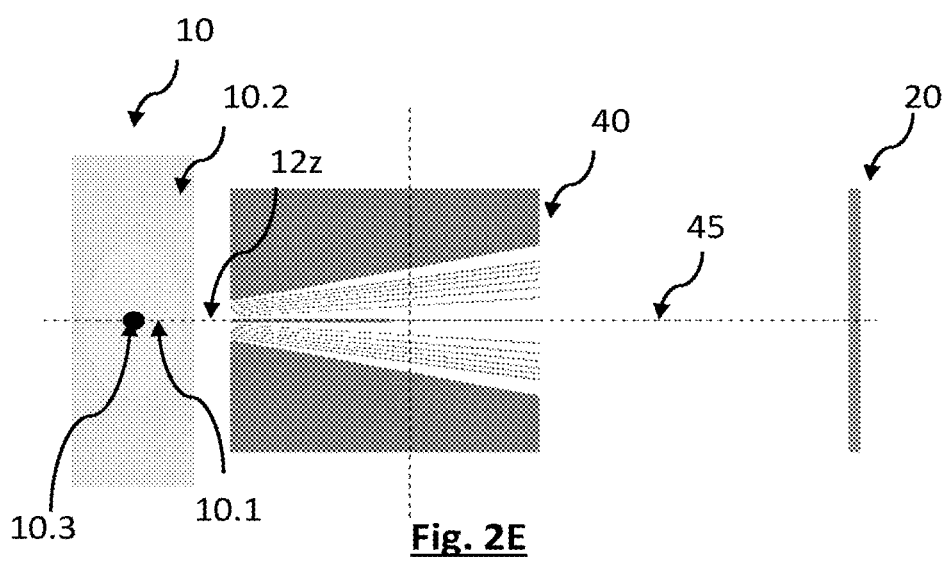

FIG. 2D is a perspective view of the device shown in FIG. 2A: the object 10, the collimator 40, the detector 20 and rays 14 scattered by the object 10 under the effect of the radiation by the collimated beam 12c, may be seen. FIG. 2E is a cross-sectional view of FIG. 2D, the cross-sectional plane passing through the central axis 45 of the collimator 40 and being parallel to this central axis. In this example, the object is composed of a fibroglandular tissue 10.1 included in a matrix 10.2 corresponding to adipose tissue. The object lastly includes a carcinoma 10.3 represented by a black spot.

Figure 3:
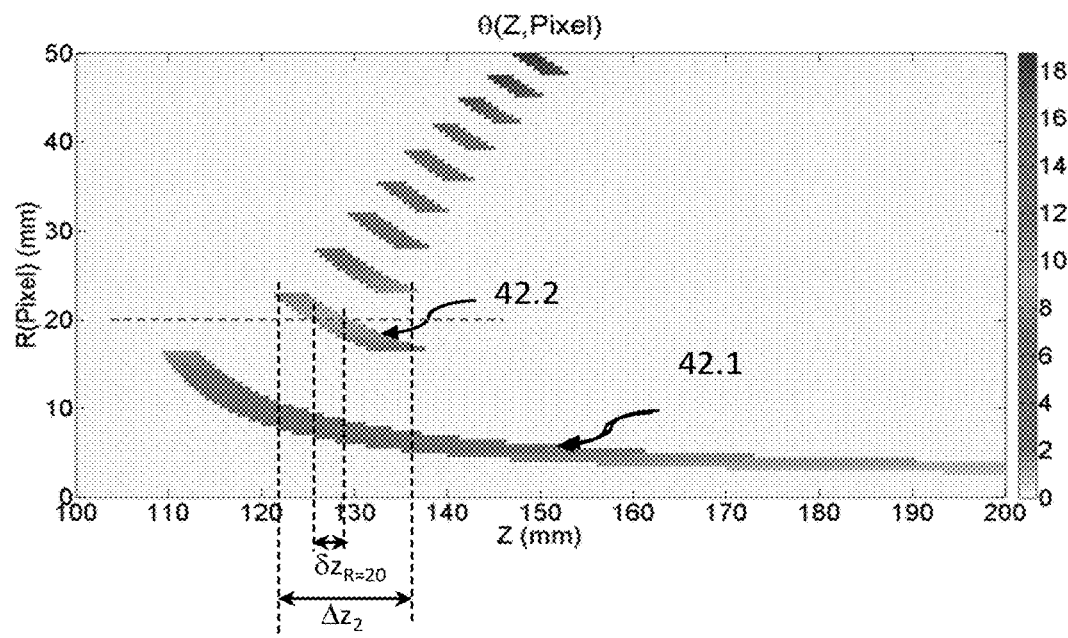
FIG. 3 shows a characterization of a collimator of similar geometry to the collimator shown in FIGS. 2A to 2E, and including 10 annular channels.

FIG. 3 shows a characterization of a collimator similar to that shown in FIGS. 2A to 2E, including 10 annular channels. This collimator is made of Denal, consisting essentially of more than 90% tungsten with nickel, iron and cobalt making up the rest. It extends, between a first plane $P_{40.1}$, which is adjacent the object, and a second plane $P_{40.2}$, which is adjacent the detector, over a height of 100 mm. The first and second planes $P_{40.1}$ and $P_{40.2}$ are placed making contact with the object and the detector ($d_1 = d_2 = 0$), respectively. Level with the first plane $P_{40.1}$, the median axes of the channels $42_1$, $42_2$, $42_3$, $42_4$, $42_5$, $42_6$, $42_7$, $42_8$, $42_9$, $42_{10}$ are spaced apart from the central axis 45 by 1.6 mm, 4.3 mm, 6 mm, 7.5 mm, 8.9 mm, 10.4 mm, 11.9 mm, 13.4 mm, 14.8 mm and 16.2 mm, respectively. The aperture of each channel is equal to 0.5 mm. Level with the second plane $P_{40.2}$, the collimator includes a solid central wall (or base wall) of 5 mm diameter, forming a cylinder around the central axis. It also includes lateral walls $41_1$, $41_2$, $41_3$, $41_4$, $41_5$, $41_6$, $41_7$, $41_8$, $41_9$, $41_{10}$ lying at a distance from the central axis 45 equal to 16.5 mm, 23 mm, 28 mm, 32 mm, 35.5 mm, 39 mm, 42 mm, 45 mm, 47.5 mm and 50 mm, respectively.

Calculations have allowed the angular range addressed by each channel $42_n$ to be determined. The abscissa represents the distance z with respect to the detector, along the Z axis, the detector being located at z=0. The scattering angles are indicated according to the colour scale shown next to this figure. It may be seen that, except for the channel $42_1$ closest to the central axis 45 of the collimator, each channel $42_n$ addresses an angular range $\Delta\theta_n$ extending over about 1° for the channels furthest from the central axis, up to a few degrees for the closest channels. For example, the angular range associated with the channel $42_2$ is comprised between 6° and 10°. The abscissa allows the spatial extension $\Delta z_n$ addressed by each channel $42_n$ along the central axis 45 of the collimator to be measured, such a spatial extension having being defined with reference to FIG. 1C. The spatial extension $\Delta z_2$ corresponding to the channel $42_2$ has been shown. The channel $42_1$ closest to the collimator has a large spatial extension, because of the small angles addressed by this channel, said angles being comprised between a few tenths of a degree and 4 degrees.

This figure also allows, for each pixel located at a radial distance R from the central axis 45, the scattering angle $\theta_R$ addressed and the distance z, with respect to the detector, to be determined, thereby allowing the volume element $\delta V_R$ of the object 10 seen by the pixel to be determined. The ordinate represents the radial distances R, the latter varying between a few mm (pixels closest to the central axis 45) and 50 mm, this corresponding to the half-width of the detector. For example, each pixel located at a radial distance R=20 mm from the axis of the collimator 45 detects scattered radiation transmitted by a volume element $\delta V_R$ of the object 10 located, along the propagation axis $12_z$ of the collimated beam $12_c$, in a distance range $\delta z_{R=20}$ comprised between 126 mm and 130 mm from the detector, this radiation being emitted at a scattering angle $\theta_R$ comprised between 8 and 9°.

Figure 4:
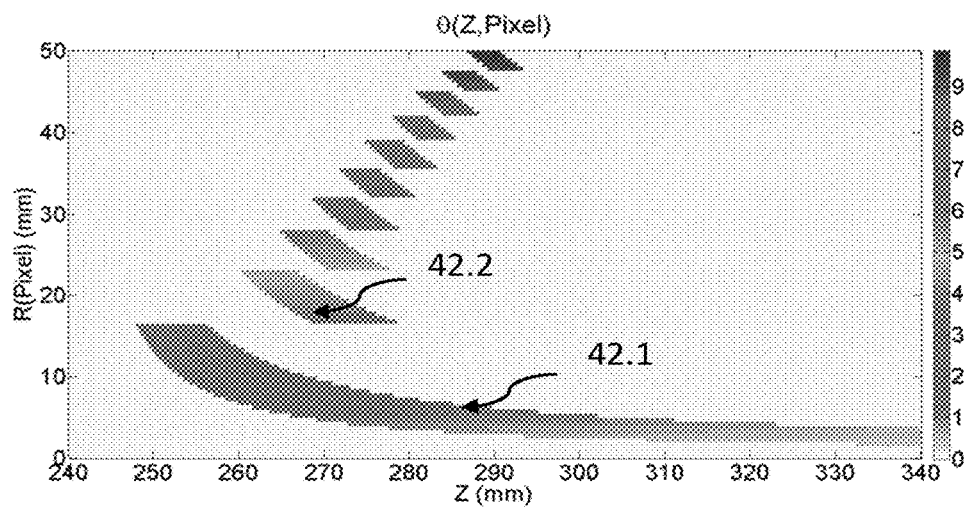
FIG. 4 shows a characterization of a collimator of similar geometry to the collimator shown in FIGS. 2A to 2E, and including 10 annular channels, this collimator extending over a larger height than the collimator characterized in FIG. 3.

FIG. 4 shows an analogous model, produced using a similar collimator to that described in the preceding example, but the height of which reaches 240 mm. The dimensions of each channel, at its first end $46_n$ and its second end $47_n$, are similar to those described in the preceding example. This collimator extends over a height of 240 mm and is placed in contact with the object and the detector. For each channel $42_n$ except for the first channel $42_1$ closest to the central axis 45 of the collimator, the angular range $\Delta\theta_n$ and the spatial extent $\Delta z$ about the central axis 45 of the collimator are observed to decrease. It will be understood that such a collimator allows the examined object to be more finely meshed, and the elementary volumes $V_n$ associated with each channel $42_n$ to be better separated. Just like FIG. 3, this figure allows the addressed scattering angle $\theta_R$ and the distance z, with respect to the detector, defining the volume element $\delta V_R$ of the object seen by each pixel located at a radial distance R from the axis of the collimator 45 to be grasped.

FIGS. 3 and 4 show that, depending on their radial distance R with respect to the axis of the collimator 45, the various pixels of the detector allow the object to be observed over a total depth of 30 to 40 mm, this depth being determined without taking into account the first channel $42_1$ closest to the axis of the collimator 45, the latter addressing a larger depth because the collimating angle $\theta_1$ is small. This confirms the advantage of such a collimator, allowing an object to be characterized over a substantial depth, without relative movement of the object and the detector.

A method allowing an object 10 to be analysed using the device 1 and a collimator such as described above will now be described.

Just as in FIG. 1A, the collimator 40 is placed such that its central axis 45 is coincident with the axis 12z along which the collimated incident beam 12c propagates. The detector 20 extends perpendicularly to the central axis 45. Under the effect of Rayleigh elastic scattering, some of the incident radiation $12_c$ is scattered at an acute angle θ to the axis $12_z$, such that $$2d\sin\left(\frac{\theta}{2}\right) = n\frac{hc}{E}, \qquad (1)$$

where:
- d is a distance characteristic of the atomic or molecular arrangement of a material making up the object. When the analysed material is a crystal, d corresponds to the interplanar spacing;
- E is the energy of the scattered radiation, expressed in keV;
- θ is the scattering angle with respect to the path of unscattered radiation; and
- h and c are Planck's constant and the speed of light, respectively.

It is common to express a quantity, referred to as the momentum transfer, represented by the letter x and expressed in $nm^{-1}$, such that:

$$\chi = \frac{\sin\left(\frac{\theta}{2}\right)E}{hc} = \frac{n}{2d}. \qquad (2)$$

To each pixel $20_{i,j}$, and a fortiori to each virtual pixel $20^*_{k,l}$, of the detector 20 there corresponds a scattering angle θ corresponding to the most probable angle at which scattered radiation 14 will reach the pixel. The advantage of the sur-pixelation is that pixels of small size are obtained, thereby decreasing the angular range of the scattered radiation liable to reach them. Specifically, by decreasing the size of the pixels, the size of each solid angle $\delta\Omega_{ij}$ under which a pixel sees the object is decreased. The sub-pixelation is therefore advantageous because it allows virtual pixels $20^*_{k,l}$ of small size to be obtained.

Since the detector 20 extends perpendicularly to the central axis 45 of the collimator 40, the locations of the pixels $20_{i,j}$ or the virtual pixels $20^*_{k,l}$ associated with a given scattering angle have an annular arrangement. These pixels form a group of pixels $20_R$, each pixel of this group addressing a given volume element $\delta V_R$ of the object 10. The pixels of a given group of pixels are located at the same radial distance R from the central axis 45 of the collimator. The association of a pixel with a volume element designates the fact that the scattered radiation received by this pixel will have mainly come from this volume element $\delta V_R$.

Figure 5:
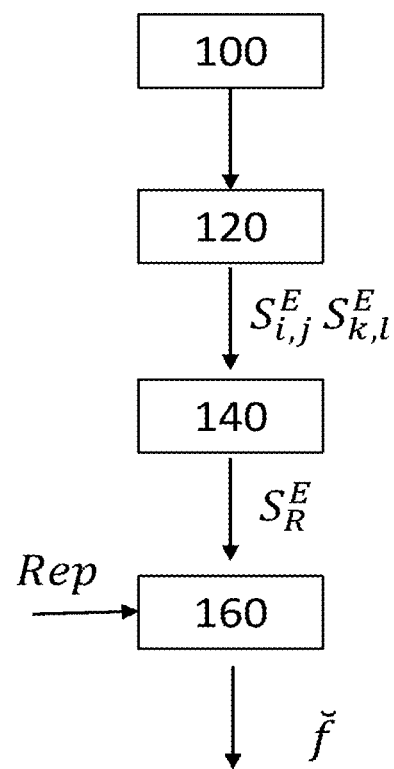
FIG. 5 shows the main steps of a method allowing an object to be analysed with a device such as shown in FIG. 1A.

The method for analysing materials then comprises the following steps, which are described with reference to FIG. 5.

a) a step in which the object 10 is irradiated by the radiation source 11, preferably through the pre-collimator 30 allowing the object to be irradiated by a collimated incident beam 12 the beam propagating along a propagation axis $12_z$. This corresponds to step 100 in FIG. 5.

b) a step in which each pixel $20_{i,j}$ of the detector, or preferably each virtual pixel $20^*_{k,l}$, acquires an energy spectrum $S_{i,j}^E$ (or $S_{k,l}^E$) of radiation 14 scattered by the object 10, each pixel (or each virtual pixel) being associated with a volume element $\delta V_R$ in the object. Preferably, each volume element is addressed by more than one pixel. This corresponds to step 120 in FIG. 5.

c) a step in which a plurality of groups of pixels $20_R$ are defined, each group of pixels including pixels receiving scattered radiation coming from a given volume element $\delta V_R$ in the object 10, said volume element being located on the propagation axis $12_z$, two different groups of pixels $20_R$, $20_R'$ receiving radiation scattered by two different volume elements $\delta V_R$, $\delta V_R'$ respectively located at two different distances z, z' from the detector; in this example, each group of pixels corresponds to the pixels located at the same radial distance R from the central axis of the collimator (45).

d) a step in which each spectrum ($S_{i,j}^E$ or $S_{k,l}^E$) corresponding to the pixels ($20_{i,j}$, $20^*_{k,l}$) located in each group are combined, so as to form an energy spectrum $S_R^E$, which is called the combined energy spectrum, representative of said group, each combined energy spectrum corresponding to one volume element $\delta V_R$ in the object. This corresponds to step 140 in FIG. 5. The combination may be a simple addition of all the spectra of the pixels of a given group.

e) a step in which a nature of the material constituting a plurality of volume elements ($\delta V_R$, $\delta V_R'$) of said object is determined using the various combined spectra. This corresponds to step 160 in FIG. 6.

With each volume element $\delta V_R$ there may be associated a distance z with respect to the detector. Each volume element $\delta V_R$ is located on the propagation axis $12z$ of the incident collimated beam $12c$. To each volume element $\delta V_R$ there corresponds a scattering angle $\theta_R$ corresponding to the angle at which scattered radiation propagates between the volume element $\delta V_R$ and each pixel of the group of pixels.

The method then allows the nature of the materials constituting the volume elements $\delta V_R$, lying at various distances z from the detector, to be deduced.

Step 160 may be implemented as follows: this step assumes a response matrix, denoted Rep, has been established, said matrix containing the spectra obtained by each pixel located at a radial distance R from the central axis of the collimator, when a material i is located at a distance z from the detector. Each term Rep(E, R, z, i) of this matrix represents a number of photons detected at the energy E by a pixel located at a radial distance R from the central axis of the collimator, when a material i is located at a distance z from the detector.

This response matrix comprises $N_E \times N_R$ rows and $N_z \times N_i$ columns, where $N_E$, $N_R$, $N_z$ and $N_i$ are respectively the number of energy channels of each spectrum, the number of radial distances R, the number of distances z and the number of materials i in question.

The various combined spectra $S_R^E$ obtained for the $N_R$ radial distances R with respect to the central axis of the collimator, may be concatenated to form a vector S, called the overall spectrum, of $N_E \times N_R$ size. Each term S(E, R) of the vector S represents a number of photons detected, at the energy E, by a pixel located at a radial distance R from the central axis of the collimator.

The method aims to determine a proportion f(z, i) of the material i at the distance z from the detector, i.e. to determine a vector f of the proportions, of ($N_z \times N_i$, 1) size, each term of which is a proportion f(z, i).

Thus, S=Rep*f, (3), where * designates matrix multiplication, each term S(E,R) of the vector S being such that:

$$S(E,R) = \Sigma_{z,i} \text{Rep}(E,R,z,i) \cdot f(z,i) \qquad (4)$$

The matrix Rep is determined in a calibrating step, carried out:
- either using experimental measurements, the object being replaced by known standard materials;
- or by simulation, using computational codes simulating the path of photons through the material;

or by combining experimental measurements and simulations.

Such a calibrating step is a conventional procedure.

The vectors S, f and the matrix Rep are written out componentwise as follows:

$$S(E, R) = \begin{bmatrix} S^E_{R=Rmin}(Emin) \\ \vdots \\ S^E_{R=Rmax}(Emax) \end{bmatrix}; f(z, i) = \begin{bmatrix} f(zmin, imin) \\ \vdots \\ f(zmax, imax) \end{bmatrix};$$

$$Rep = \begin{bmatrix} Rep(E = Emin, R = Rmin, & & Rep(E = Emin, R = Rmin, \\ z = zmin, i = imin) & \cdots & z = zmax, i = imax) \\ \vdots & \ddots & \vdots \\ Rep(E = Emax, R = Rmax, & & Rep(E = Emax, R = Rmax, \\ z = zmin, i = imin) & \cdots & z = zmax, i = imax) \end{bmatrix}$$

where Emin, Rmin, zmin and imin respectively designate the minimum indices of E, R, z and i, and Emax, Rmax, zmax and imax respectively designate the maximum indices of E, R, z and i.

Having determined the response matrix Rep, and having obtained the overall spectrum S from the measurements, it is possible to obtain an estimation $\hat{f}$ of the vector of the compositions f using a reconstruction algorithm. Among commonly used iterative reconstruction algorithms, a MLEM algorithm (MLEM standing for maximum likelihood expectation maximization) may be used. According to such an algorithm, the value of each term of the vector $\hat{f}^q$ may be obtained using the following expression:

$$\tilde{f}^q(z, i) = \tilde{f}^{q-1}(z, i) \frac{1}{\sum_{E,R} Rep(E, R, z, i)} \sum_{E,R} \frac{Rep(E, R, z, i) \cdot S(E, R)}{\sum_{Z,i} Rep(E, R, z, i) \cdot \tilde{f}^{q-1}(z, i)} \quad (5)$$

the exponent q designating the rank of each iteration.

According to one embodiment, the method includes a step of changing variable, in which each spectrum $S_{i,j}^E$ is converted using equation (2) into a spectrum $S_{i,j}^X$ representing a distribution of the momentum transfer, the angle θ corresponding to the angle θ associated with the pixel $20_{i,j}$ (or the virtual pixel $20^*_{k,l}$ where appropriate). Such a spectrum is not an energy spectrum, but indeed remains a spectrum representative of the energy distribution of said detected radiation.

The invention will possibly be used to provide data necessary to make a diagnosis. For example, it will possibly be implemented on suspect zones detected beforehand by an imaging method such as x-ray radiography, x-ray tomography, echography or MRI. This allows an in vivo characterization of tissues considered to be suspect to be obtained, and the need to use more invasive, and more traumatizing, techniques such as biopsies to be avoided. The fact that the location is considered to be known makes it possible to concentrate on the suspect zones and to limit the integrated dose received by the patient. Specifically, using such knowledge considered to be gained, the device may be used such that the axis of the collimated beam $12_z$ passes through the suspect zone determined beforehand.

The invention will possibly also be implemented in other non-destructive material inspection applications: inspection of luggage, detection of illicit substances, inspection of the integrity of structures, etc.

The invention claimed is:

1. A Device for analysing an object, comprising:
    a radiation source configured to produce ionizing electromagnetic radiation, the radiation propagating towards a holder, the holder being able to hold the object;
    a first collimator, placed between the radiation source and the holder, the first collimator having an aperture configured to form a collimated beam propagating along a propagation axis towards the holder;
    a detector, comprising pixels, each pixel being able to detect ionizing electromagnetic radiation and to form therefrom an energy spectrum;
    a second collimator, placed between the holder and the detector, the second collimator being configured to selectively direct radiation emitted by the object, which is held by the holder, towards said detector, depending on a scattering angle of the radiation emitted by the object;
    wherein
    the second collimator extends, between a first end and a second end, around a central axis, the second collimator including a plurality of channels, each channel being bounded by lateral walls, the second collimator being such that:
        each channel has a median axis, the median axis extending, in the centre of the channel, between said lateral walls bounding the channel;
        the median axis of each channel makes an acute angle, called the collimating angle of the channel, with the central axis of the second collimator;
        each channel being associated to a point, called the focal point, formed by an intersection between the median axis of the channel and the central axis of the second collimator;
        the second collimator including at least two channels, the collimating angles of which are different, the focal points respectively associated with these channels being different and spaced apart from each other along the central axis of the second collimator;
    such that each channel transmits to the detector a radiation emitted by an elementary volume of the object, which is placed on the holder, extending around a focal point defined by the second collimator, in a preset angular range.

2. The Device according to claim 1, wherein the second collimator comprises a plurality of channels having the same collimating angle, the channels extending around the central axis of the second collimator, the focal points of the channels being coincident.

3. The Device according to claim 1, wherein at least one channel has a cross section in a plane perpendicular to the central axis, the cross section forming all or some of a ring around the central axis of the second collimator.

4. The Device according to claim 3, wherein at least one ring is circular or polygonal.

5. The Device according to claim 1, wherein at least two focal points are spaced apart, along the central axis of the second collimator, by a distance larger than 2 cm.

6. The Device according to claim 1, wherein each lateral wall bounding a channel of the second collimator is produced from a material the atomic number of which is higher than 26.

7. The Device according to claim 1, wherein each channel of the second collimator is bounded by a lateral wall called the proximal wall and a lateral wall called the distal wall, the proximal wall being closer to the central axis than the distal wall, and wherein each of these walls extends, between the first end of the channel and the second end of the channel, in such a way as to form a frustoconical area defined:
- by an apex, located on the central axis;
- and, at said second end, by a generatrice describing all or some of a ring.

8. The Device according to claim 1, wherein the second collimator includes what is called a base wall extending around the central axis and describing a cylinder or conical frustum, of thickness larger than 5 mm.

9. The Device according to claim 1, wherein the second collimator is placed such that its central axis is coaxial with the propagation axis of the collimated incident beam.

10. The Device according to claim 1, wherein the detector extends in a plane perpendicular to the central axis of the second collimator.

11. The Device according to claim 1, wherein the detector is connected to a microprocessor able to subdivide each pixel of the detector into virtual pixels, and wherein a plurality of pixels or virtual pixels are placed in the extension of a given channel.

12. A Method for characterizing an object using a device according to claim 1, comprising the following steps:
a) placing the object on the holder of the device and irradiating the object using the irradiation source, so as to form a collimated incident beam propagating towards the object along a propagation axis, the object being placed such that a plurality of focal points, which are defined by the second collimator, are placed in said object;
b) using each pixel of the detector, detecting radiation scattered by the object following its radiation by said collimated incident beam and forming a spectrum representative of the energy distribution of said detected radiation;
c) defining a plurality of groups of pixels, each group of pixels receiving radiation scattered by a given volume element of the object, the volume element being located on the propagation axis, two different groups of pixels receiving radiation scattered by two different volume elements;
d) for each group of pixels defined in the preceding step, combining the spectrum acquired by each pixel, so as to establish a spectrum, called the combined spectrum, associated with said group of pixels; and
e) using the combined spectra respectively associated with various groups of pixels, determining a nature of the material constituting a plurality of volume elements of the object.

13. The Method according to claim 12, wherein
the central axis of the second collimator is coincident with the propagation axis of the collimated beam; and
the detector extends perpendicularly to the axis of the second collimator, each group of pixels including pixels located at the same distance, called the radial distance from said central axis of the second collimator.

14. The Method according to claim 12, wherein the direction of the collimated incident beam is defined on the basis of knowledge considered to be gained by prior inspection of the object.

15. The Method according to claim 14, wherein said prior inspection is carried out by x-ray radiography, or x-ray tomography, or echography, or magnetic resonance imaging.

* * * * *